United States Patent [19]
Yaffe

[11] Patent Number: 4,638,502
[45] Date of Patent: Jan. 20, 1987

[54] ANTHROPOMORPHIC PHANTOMS

[75] Inventor: Martin J. Yaffe, Toronto, Canada

[73] Assignee: The Ontario Cancer Institute, Toronto, Canada

[21] Appl. No.: 753,025

[22] Filed: Jul. 8, 1985

[51] Int. Cl.$^4$ ............................................. G01D 18/00
[52] U.S. Cl. .................................... 378/207; 250/252.1
[58] Field of Search ....................... 378/207; 250/252.1

[56] References Cited

U.S. PATENT DOCUMENTS 3,755,672  8/1973  Edholm et al. ..................... 378/158

OTHER PUBLICATIONS

D. R. White, "Tissue Substitutes in Experimental Radiation Physics", Med. Phys. 5(6), Nov./Dec. 1978, pp. 467–479.
Brochure "The MCP-70-SE-System for Making and Applying Irregular Shields and Compensators for Radiotherapy" HEK, 1983 or earlier.

Primary Examiner—Janice A. Howell
Attorney, Agent, or Firm—Ridout & Maybee

[57] ABSTRACT

Anthropomorphic phantoms for radiological testing, assessment and training are prepared by obtaining a radiograph of a body part to be simulated, translating the radiograph into densitometric data, translating the densitometric data into thickness data representing the thickness of a selected phantom material required to produce that density under conditions similar to those used to produce the original radiograph, and using the thickness data obtained to produce, for example by employing a numerically controlled milling machine, a three dimensional representation of those thicknesses on the selected material which matches the radiographic image forming characteristics of the original body part when imaged under similar conditions.

22 Claims, 3 Drawing Figures

ANTHROPOMORPHIC PHANTOMS

FIELD OF THE INVENTION

This invention relates to radiological phantoms, particularly anthropomorphic phantoms.

BACKGROUND OF THE INVENTION

Radiological phantoms and other test objects are often used as objects to be imaged in radiological equipment for the following purposes:

(i) to compare different radiographic systems when considering equipment purchases, (ii) to standardize image quality among different facilities performing similar radiological procedures, (iii) to assist in selection of technical factors for image production, (iv) for routine quality assurance testing, and (v) for the teaching of the principles of image formation to residents and radiological technologists.

An anthropomorphic radiological phantom is designed to simulate the interaction of x rays with a particular anatomical site in the human body. A phantom should satisfy the following requirements:

(i) it should yield reproducible images when irradiated under identical conditions, i.e. it should not decompose or change its radiation attenuating characteristics with time, (ii) it should produce images which can be used to assign numerical indices of imaging performance of the system being evaluated, (iii) the images produced by the phantom should be anthropomorphic, i.e. have similar characteristics to images of human body parts which would normally be made with the system being evaluated. This is important because the radiologist who is ultimately responsible for the diagnostic quality of the images, is trained to evaluate images not by objective masurements of contrast, noise, and resolution, but by the perceptibility of anatomic structures in the body. Often such individuals have difficulties in relating results obtained using simplistic objective phantoms currently available to the quality that will be obtained in actual patient images.

There is a need for the production of anthropomorphic phantoms for radiological imaging which are more realistic than those presently available.

It is known in radiographic practice to utilize radiographic data to produce shields and compensators which are applied to patients to protect specific body parts from radiation, or to modulate radiation exposure. The data is reviewed and processed and used to cut a styrofoam mould profiled when filled with a radiation absorbent material to provide a desired pattern of attenuation to the incident radiation. The shields and protectors produced are used to control radiation dosage, not for imaging purposes, and are used in conjunction with the patient, not as a substitute.

SUMMARY OF THE INVENTION

A truly anthropomorphic phantom, when radiographed under the same radiological environment used to produce a radiograph of the human body part to be simulated, will produce an image identical to that of the human radiograph. This requires that at each point in the plane of the image receptor the energy fluence spectra of both primary and scattered x rays from the phantom be identical to those emanating from the body part in the original view. In practice this would be difficult if not impossible to achieve unless the phantom were identical in shape and composition to the body part. We have found that good results can be obtained by relaxing this requirement to one in which the integral energy fluence transmitted by the phantom must match that transmitted by the body part at each point in the plane of the image receptor and where the average fluences of scattered radiation are matched. This allows greater flexibility in the choice of phantom materials and still produces similar images provided that the phantom is irradiated in the same radiological environment as the patient.

A further consideration, tissue-equivalence, requires that the absorption and scattering properties of the body part and phantom have the same energy dependence, so that equivalence will be maintained for any x-ray spectrum to be used for imaging. Tissue equivalence is desirable if the x-ray spectrum is one of the variables to be considered in image evaluation.

According to the invention there is provided a method for producing a radiological phantom comprising obtaining a radiograph of an object to be simulated, densitometrically scanning the radiograph with a densitometer, digitizing and sampling the densitometer output at a sampling rate sufficient to produce data defining a densitometric image of the object having a defined spatial resolution, obtaining radiographic calibration data for material to be used for the phantom, such as to relate radiographic density to material thickness under conditions similar to those used for obtaining the radiograph of the object and over a range of densities comprising the density range of the object radiograph, using the calibration data to translate the densitometric data defining the image of the object into thickness data, and using said thickness data to form from the same material as the sample a three dimensional representation of the thickness data configured to overlay a radiographic image plane. The invention extends to phantoms produced by the above method.

In the context of this specification "thickness" means the path length through the phantom material of radiation passing between the radiation source and the image plane in the radiological equipment with which the phantom is to be used. Where the maximum thickness and area of the phantom are small compared with the distance of the source from the phantom, the radiation may be considered to pass through the phantom in parallel lines, but if those conditions are not met the thickness of the phantom material representing any particular pixel of the image produced by the phantom should be measured on a line extending between the actual entrance and exit points on the phantom.

Further features of the invention will become apparent from the following description with reference to the accompanying drawings, in which.

Figure 1:
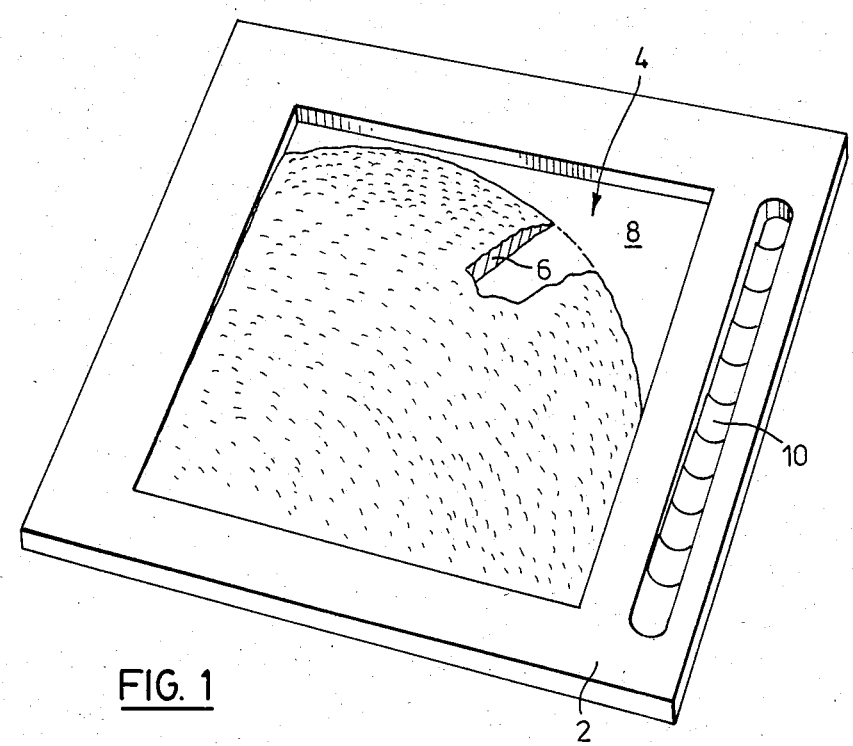
FIG. 1 is a perspective view of a first type of phantom produced by the method of the invention, partly broken away to emphasize its three dimensional character.
Figure 2:
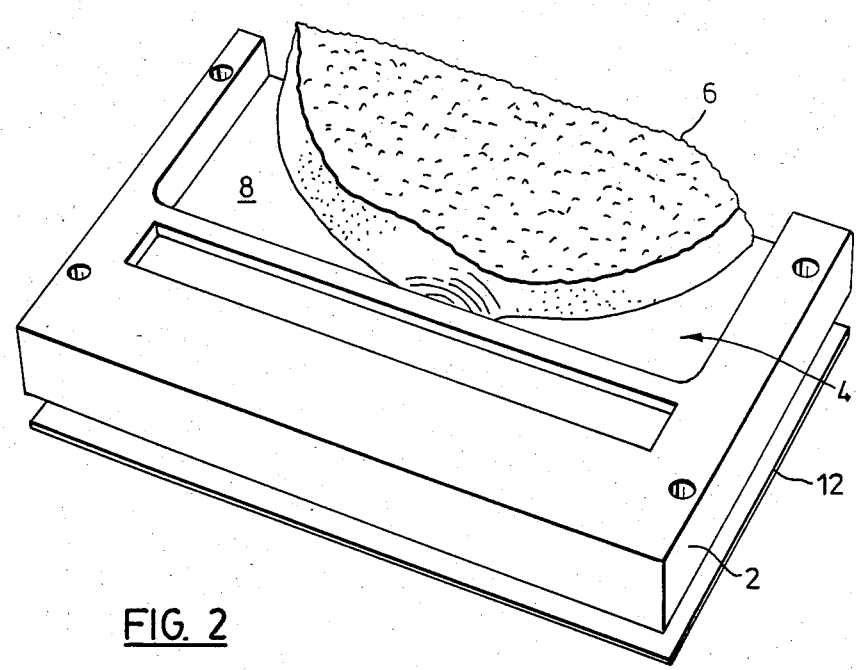
FIG. 2 is a perspective view of a second type of phantom produced by the method of the invention.

Referring to the drawings, FIGS. 1 and 2 both show anthropomorphic breast phantoms, which were derived from conventional mammograms and which can reproduce those mammograms with a high degree of verisimilitude if placed above the image plane and radiographed under similar conditions of exposure, x-ray spectrum, and reproduction medium to the originals. The phantom of FIG. 1 is relatively thin, being machined from a 6 mm thick plate of aluminum, whereas that of FIG. 2 is of substantial thickness, being machined from a block of the polymethylmethacrylate sold under the trade mark LUCITE. In each case, the phantom comprises a supporting frame 2, defining a window 4 within which the phantom proper 6 is supported. In FIG. 1, background areas 8 within the frame are open, whereas in FIG. 2 they are webs having a small uniform thickness whose opacity to radiation is low enough to fall outside the contrast range of the reproduction medium likely to be used in association with the phantom. These webs support the phantom 6 within the window. To enhance the usefulness of the phantom, the frame 2 may incorporate a thickness step wedge 10 as seen in the right hand side of the frame 2 in FIG. 1.

Figure 3:
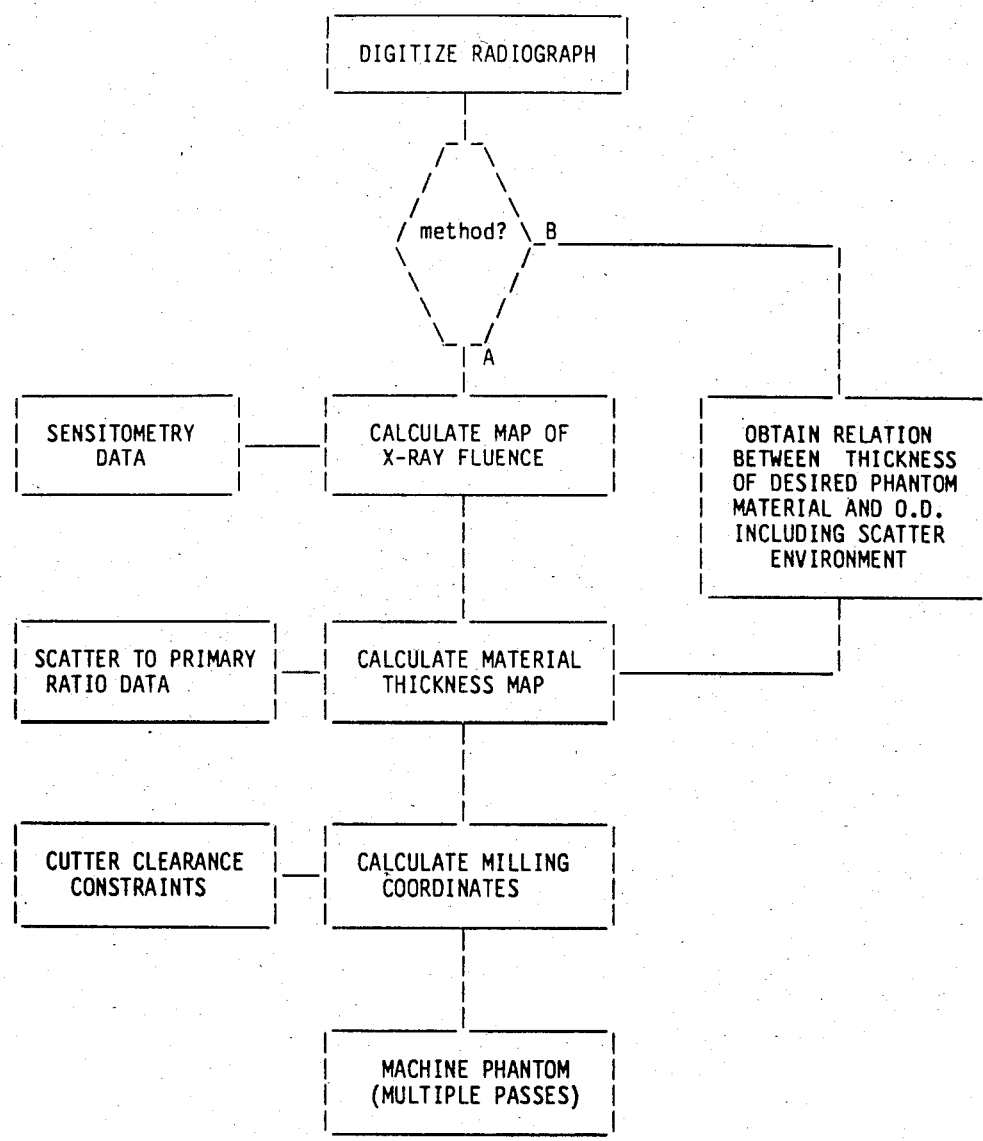
FIG. 3 is a flow diagram illustrating the method of the invention.

Referring now to the flow diagram of FIG. 3, the production of phantoms such as those described with reference to FIGS. 1 and 2 will be described.

A radiograph of the body part to be simulated is obtained, of a quality suitable for use as a standard. In order to define the radiographic environment in which the particular view of the body part was obtained, the film utilized, exposure factors, geometry and film processing parameters are all carefully noted for reference purposes. This radiograph is then digitized using a microdensitometer such as the Perkin Elmer PDS, using a raster with a spatial resolution appropriate to the resolution required for the desired phantom, i.e. sufficient that the phantom can reproduce the original radiograph with a high degree of verisimilitude when imaged in the same environment as the original. In the example shown, digitization was carried out using sampling intervals of 40 micrometers. The microdensitometer data are then converted from specular to diffuse density by scanning standard gray wedges providing a calibration to values obtained on a Macbeth densitometer. From the resultant adjusted matrix of diffuse density, two methods can be adapted to design the phantom:

A. by using (as in the phantom of FIG. 1) the sensitometric curve of the film screen combination and calculating the thickness of the phantom at each exit point to match energy fluence absorbed by the image receptor, or B. by a direct calibration (as in the phantom of FIG. 2) between film optical density and phantom thickness.

Although the former method is more elegant, the latter may be more practical. Both will be described below.

A. SENSITOMETRIC METHOD

The characteristic curve of the same film screen combination used to produce the patient radiograph was measured. This was done using x rays with the same kVp and filtration and an appropriate amount of added low atomic number attenuation to produce approximately the same spectrum at the image receptor as in the original examination. An attempt was made to maintain the same film processing parameters by measuring the curve immediately after the original exposure. A bootstrap step wedge sensitometry method was used. The curve obtained was then used to transform the adjusted matrix into matrix whose elements represent exposure at the plane of the image receptor.

A phantom material was then chosen. An experiment was performed to determine the scatter to primary ratio for the appropriate spectrum of x rays traversing various thicknesses of this material; in this example, aluminum. Alternatively, Monte Carlo data could be used if available. These data were combined with a simple calculation of primary transmission to obtain a curve relating the transmitted x-ray exposure at a cassette holding the film, including scatter, to material thickness. For this curve the simplifying assumption was made that the x-ray fluence was uniform over a plane at the entrance to the patient or phantom. It was also assumed that the exit scatter fluence at the image receptor plane was uniform and could be characterized by the behaviour of the phantom at a reference point. The reference point was, therefore, chosen in an area of the object thought to typify the overall amount of exit scatter. The appropriate thickness of the chosen phantom material required to match the fluence received at each element was then determined.

B. DIRECT METHOD

In this method a phantom material was chosen and a calibration phantom of the same material was produced. Such a phantom using polymethylmethacrylate consisted of a block of material whose thickness was variable by the addition or removal of additional sheets of the same material. Each thickness created an ambient scatter environment representative of a particular thickness and density of the originally imaged portion of human anatomy. Superimposed on the base thickness were rods and cylindrical holes which modulated the local thickness of the phantom in order to assist in obtaining the required sensitometric data in that scatter environment, the additional sheets having apertures to match those rods and holes.

When this phantom was imaged under the same conditions as those of the original radiograph using different thicknesses, curves were obtained relating phantom thickness and optical density, with each curve representing a different base thickness. By interpolation, a base thickness was chosen that provided a match of average optical density between the phantom image and the original radiograph. The appropriate calibration curve was then applied to the adjusted matrix data to obtain a matrix of required phantom thicknesses.

In the next step, the path of a milling machine cutter required to produce the needed thickness modulation in the phantom material was calculated. Since the phantom has to reproduce subtle attenuation variations at high spatial resolution, it is desirable to use the finest possible cutting tool. It was found that a practical approach to this requirement was to remove as much extraneous material as possible with an initial pass with a larger cutter. For this pass, a raster line "terracing" technique was used where the tool path between adjacent (x,y) coordinates lay at a constant value of depth, z. As well, an algorithm was used to guide the milling path which considered the three dimensional space occupied by the cutter and tool holder and calculated the cutting coordinates such that the space occupied by material required to be left intact was never encroached upon. In this way it was ensured that material required for a subsequent pass at higher resolution was left intact.

The coordinates for milling were then translated into a program in the code required to drive a numerically controlled milling machine and the cutting program was transferred to the milling machine via a microprocessor based interface. The interface was equipped with 256 kbytes of memory so that large cutting files could be transferred efficiently from a main time shared computer used to carry out the various calculations.

The actual machining was done using ball nosed milling cutters with a final cut performed with carbide dental burrs. The time required to produce a phantom depends on the desired spatial resolution and the material used but is typically in excess of ten hours.

For multiple phantoms a negative impression is formed from the original in any material suitable for forming a mould which can be used for casting phantoms in the selected material.

Tests showed that both phantoms were capable of producing, when imaged under the same conditions as the original mammograms used for the production, radiographs which were excellent facsimiles of the original. The phantom of FIG. 2 however had energy dependent imaging properties more like those of the original body part than that of FIG. 1. Since the thickness of the plastic phantom of FIG. 2 was much greater than the metal phantom of FIG. 1, it was necessary to allow during design for beam divergence through the phantom, and for variations in intensity over the entrance surface of the phantom, since it could no longer be assumed that the source distance was effectively infinite or that differences in path length to source were insignificant. Still closer simulation of the radiographic characteristics of body parts may be obtained by selecting materials whose radiographic characteristics more closely resemble appropriate types of human tissue, and in some cases a composite phantom comprising layers of materials of the same or different densities may be utilized. Thus it may be advantageous to process the sensitometer data to obtain various forms of segregation. For example, the data may be processed to separate it into densities up to a certain maximum, and densities above that maximum, and to produce separate phantom elements possibly using materials of different electron density and atomic number, which are overlaid to obtain the finished phantom. This technique is of value in cases where the rate of thickness change might otherwise be so great as to render machining difficult. Where a substantial area has a significant minimum density, it may be advantageous to utilize a thickness or loading film 12 (see FIG. 2), such as a photographic film of a uniform degree of opacity, as an underlay to represent this minimum density, thus reducing the overall thickness the phantom. To speed machining, it may be advantageous in some instances to machine separate phantom elements to represent coarse and fine detail, or to represent the fine detail as density variations of a photographic film underlay 12.

In addition to the step wedge shown in FIG. 1, other test configurations such as low and high resolution test patterns and contrast detail phantoms can be machined into the phantom.

Although the invention has been described as applied to a breast phantom, it may of course be applied to phantoms of other body parts.

I claim:

1. A method for producing a radiological phantom comprising obtaining a radiograph representing a radiographic image of a particular view of a body part to be simulated in a defined radiographic environment, densitometrically scanning the radiograph with a densitometer, digitizing and sampling the densitometer output at a sampling rate sufficient to produce data defining a densitometric image of the body part having a spatial resolution sufficient that the phantom can substantially reproduce the original radiograph when imaged in the same environment, obtaining the phantom, such as to relate radiographic density to material thickness in the radiographic environment used for obtaining the radiograph and over a range of densities comprising the density range of the radiograph, using the calibration data to translate the densitometric data defining the image into thickness data, and using said thickness data to form from the same material as the sample a three dimensional representation of the thickness data configured to overlay a radiographic image plane and to produce in said defined radiographic environment an image similar to that which would have been produced by said particular view of the original body part in that environment.

2. The method according to claim 1, wherein the calibration data is obtained by producing a calibration radiograph of a sample of the material to be used for the phantom, the sample being radiographed under conditions similar to those used for obtaining the radiograph of the body part, and having a range of defined thicknesses providing a range of densities in the calibration radiograph, and determining calibration data relating density to sample thickness from the calibration radiograph.

3. A method according to claim 2, wherein the sample has a series of projections and recesses modulating its thickness to assist in determining the calibration data, and a thickness which is variable by the addition and removal of additional sheets of material.

4. A method according to claim 1, wherein the calibration data is derived by determining the sensitometric curve of the image receptor and medium used to produce the radiograph and calculating the thickness of the phantom material required to match a particular level of energy fluence absorbed by the image receptor.

5. A method according to claim 1, wherein a correction is applied to the calibration data to allow for scatter, based upon an area of the radiograph selected to typify the overall amount of exit scatter.

6. A method according to claim 1, wherein the densitometric data is segregated and used to form independent phantom components which are combined to provide the finished phantom.

7. A method according to claim 6, wherein the densitometric data is segregated to provide densitometric image data relating to different ranges of density.

8. A method according to claim 6, wherein one of the phantom components is formed by a photographic film having an opacity representing one of the segregated groups of the data.

9. A method according to claim 8, wherein the segregated group of data represented by the photographic film is the fine detail of the original radiograph.

10. A method according to claim 1, wherein the thickness data is applied to a numerically controlled milling machine which cuts the phantom material to form the required three dimensional representation.

11. A method according to claim 1, wherein the thickness data is first used to form a mould having a configuration complementary to that of the desired three dimensional representation, and the mould is used to form the phantom.

12. A method according to claim 1, wherein a material used for the phantom is selected to have radiographic characteristics similar to a type of human tissue to be represented by the phantom.

13. A radiological phantom simulating a body part, comprising a body of material having a thickness modulated by densitometric data derived from a radiograph of an actual body part such that, in a defined radiological environment matching that in which the original radiograph was produced, an integral energy fluence pattern, matching that of the radiograph, is obtained on a point to point basis in the plane of an image receptor, and average fluences of scattered radiation are substantially matched, whereby a radiograph of the phantom will be substantially the same as said radiograph of the original body part if the radiological environment is the same.

14. A phantom according to claim 13, wherein the phantom comprises a block or sheet of homogeneous material having an entry surface contoured to provide the required modulation of its thickness.

15. A phantom according to claim 14, wherein the phantom is of aluminum.

16. A phantom according to claim 14, wherein the phantom is of a synthetic resin.

17. A phantom according to claim 16, wherein the synthetic resin is polymethylmethacrylate.

18. A phantom according to claim 14, wherein the body part simulated is a human breast.

19. A phantom according to claim 13, including a photographic film underlying the body and representing a segregated portion of densitometric data derived from said radiograph.

20. A phantom according to claim 19, wherein the film is a loading film of a uniform degree of opacity, representing a minimum density of at least a substantial area of the original radiograph.

21. A phantom according to claim 19, wherein the segregated data represented by the film is fine detail of the original radiograph.

22. A phantom according to claim 13, wherein the material of the phantom is selected to have radiographic characteristics similar to a type of human tissue to be represented by the phantom.

* * * * *